US008637486B2

(12) United States Patent
Shchepinov

(10) Patent No.: US 8,637,486 B2
(45) Date of Patent: Jan. 28, 2014

(54) THERAPEUTIC SUBSTANCES THAT MODULATE GENOME METHYLATION

(75) Inventor: Mikhail S. Shchepinov, Kingston upon Thames (GB)

(73) Assignee: Retrotope, Inc., Los Altos Hills, CA (US)

( * ) Notice: Subject to any disclaimer, the term of this patent is extended or adjusted under 35 U.S.C. 154(b) by 426 days.

(21) Appl. No.: 12/922,439

(22) PCT Filed: Mar. 13, 2009

(86) PCT No.: PCT/US2009/037173
§ 371 (c)(1),
(2), (4) Date: Dec. 7, 2010

(87) PCT Pub. No.: WO2009/114814
PCT Pub. Date: Sep. 17, 2009

(65) Prior Publication Data
US 2011/0082100 A1 Apr. 7, 2011

Related U.S. Application Data

(60) Provisional application No. 61/036,882, filed on Mar. 14, 2008.

(51) Int. Cl.
*A61K 31/70* (2006.01)
(52) U.S. Cl.
USPC ............. 514/49; 514/45; 536/28.1; 536/28.4; 536/28.5; 536/28.8
(58) Field of Classification Search
USPC .................. 514/45, 49; 536/28.1, 28.5, 28.8, 536/28.51–28.55
See application file for complete search history.

(56) References Cited

U.S. PATENT DOCUMENTS

| | | | |
|---|---|---|---|
| 3,520,872 | A | 7/1970 | Wechter et al. |
| 6,211,166 | B1 * | 4/2001 | Hattori et al. ................ 514/49 |
| 6,221,335 | B1 | 4/2001 | Foster |
| 6,340,578 | B1 * | 1/2002 | Anderson et al. ............ 435/71.1 |
| 6,603,008 | B1 | 8/2003 | Ando et al. |
| 8,221,769 | B2 * | 7/2012 | Szalay et al. ............... 424/232.1 |
| 2006/0035382 | A1 | 2/2006 | Shinozaki et al. |
| 2006/0205685 | A1 | 9/2006 | Phiasivongsa et al. |
| 2007/0082929 | A1 * | 4/2007 | Gant et al. .................... 514/338 |
| 2009/0069354 | A1 | 3/2009 | Czarnik |
| 2009/0105184 | A1 * | 4/2009 | Radu et al. ..................... 514/45 |
| 2010/0160248 | A1 | 6/2010 | Shchepinov |

FOREIGN PATENT DOCUMENTS

| | | |
|---|---|---|
| FR | 2721518 | 12/1995 |
| JP | 2000-290291 | 10/2000 |
| JP | 2002-513911 | 5/2002 |
| JP | 2002-536981 | 11/2002 |
| WO | WO2007102030 | 9/2007 |
| WO | WO2009114814 | 9/2009 |

OTHER PUBLICATIONS

Tonn et al., Synthesis of Deuterium-labeled Elliptinium and its use in Metablic Studies, Biomedical and Environemntal Mass Spectrometry, 1988, vol. 15, 243-247.*
Wolen et al., The Application of Stable Isotopes to Studies of Drug Bioavailability and Bioequivaence, J Clin. Pharmacol, 1985, vol. 25, 419-424.*
Balasubramanian et al; DNA strand breaking by the hydroxyl radical is governed by the accessible surface areas of the hydrogen atoms of the DNA backbone. Proc. Natl. Acad. Sci. USA, Aug. 1998, vol. 95 pp. 9738-9743.
Burdzy et al; Synthesis of stable-isotope enriched 5-methylpyrimidines and their use as probes of base reactivity in DNA, Nucleic Acids Research, 2002, vol. 30, No. 18, pp. 4068-4074.
Chiriac et al; Synthesis of [1,3,6,7-15N, 8-13C] adenine; Journal of Labelled Compounds and Radiopharmaceuticals; Apr. 1999 (published online May 4, 1999); vol. 42, issue 4, pp. 377-385.
Dalle-Donne et al; Protein carbonylation in human diseases; Trends in Molecular Medicine; Apr. 2003, vol. 9, No. 4, pp. 169-176.
Demidov,V.; Heavy isotopes to avert ageing?; Trends in Biotechnology; Aug. 2007, vol. 25, No. 9, pp. 371-375.
Esaki et al; Synthesis of base-selectively deuterium-labelled nucleosides by the Pd/C-Catalyzed H-D Exchange Reaction in Deuterium Oxide; Heterocycles; 2005; vol. 66, pp. 361-369.
Foldesi et al; The Synthesis of Deuterionucleosides; Nucleosides, Nucleotides and Nucleic Acids; 2000, vol. 19, No. 10-12, pp. 1615-1656.
International Search Report and Written Opinion dated Sep. 10, 2010 for PCT/US2009/037173.
International Search Report dated Jun. 12, 2007 for PCT/GB2007/050112.
Kishore et al; Partial 13C Isotopic Enrichment of Nucleoside Monophosphates: Useful Reporters for NMR Structural Studies; Nucleic Acids Research; Oct. 2005, vol. 33, No. 18.
Kushner et al; Pharmacological uses and perspectives of heavy water and deuterated compounds; Canadian Journal of Physiology and Pharmacology; Feb. 1999; vol. 77, pp. 79-88.
Shchepinov, Mikhail; Reactive Oxygen Species, Isotope Effect, Essential Nutrients, and Enhanced Longevity; Rejuvenation Research; 2007; vol. 10, No. 1, pp. 47-59.
Svedruzic et al; The Mechanism of Target Base Attack in DNA Cytosine Carbon 5 Methylation; Biochemistry; Aug. 2004; vol. 43, No. 36, pp. 11460-11473.
The Aldrich Catalog Handbook of Fine Chemicals 2003-2004, p. 141, catalog No. 48, 998-0.
Toyama et al; Assignments and hydrogen bond sensitivities of UV resonance Raman bands of the C8-deuterated guanine ring; Journal of Raman Spectroscopy; Sep. 2002; vol. 33, issue 9, pp. 699-708.

(Continued)

*Primary Examiner* — Michael G Hartley
*Assistant Examiner* — Jagadishwar Samala
(74) *Attorney, Agent, or Firm* — Knobbe Martens Olson & Bear LLP

(57) ABSTRACT

Compounds containing nucleic acid bases or their precursors modified by enrichment at specific sites with heavy stable isotopes of elements naturally present at those sites in minute amount are useful for the treatment of diseases characterized by altered gene expression and altered pattern of epigenomic control. These compounds, when used as nutrients or in other medicinal application methods, can alter the DNA methylation pattern in a simple way through the well-understood mechanism of kinetic isotope effect (KIE). This effect could also be useful for modifying methylation kinetics in stem cell technology, cloning and as disease therapeutics.

14 Claims, No Drawings

(56) References Cited

OTHER PUBLICATIONS

Wade, David; Deuterium isotope effects on noncovalent interactions between molecules; Chemico-Biological Interactions; 1999; vol. 117, No. 3, pp. 191-217.

Written Opinion dated Sep. 8, 2008 for PCT/GB2007/050112.

Chen et al, One-pot selective deuteriation of 5'-dimethoxytritylated deoxynucleotide derivatives, Bioorganic & Medicinal Chemistry Letters, Pergamon, Elsevier Schince, GB, vol. 4, No. 6, pp. 789-794, Mar. 24, 1994.

Extended European Search Report dated Jul. 12, 2011 for EP Application No. 09721095.

Wheeler et al, The synthesis of the 2H, 3H, and 14C-isotopomers of 2'-deoxy-2', 2'-diflourocytidine hydrochloride, an anti-tumor compound, Journal of labelled compounds and radiopharmaceuticals, John Wiley, Chichester, GB, vol. 29, No. 5, pp. 583-589, May 1, 1991.

Finglas et al, Use of an oral/intravenous dual-label stable-isotope protocol to determine folic acid bioavailability from fortified cereal grain foods in women, The Journal of Nutrition, vol. 132, No. 5, pp. 936-939, May 2002.

Notice of Reasons for Rejection dated Aug. 24, 2011 for Japanese Patent Application No. 2008-557833.

Baillie, Thomas; The Use of Stable Isotopes in Pharmacological Research, Pharmacological Reviews, vol. 33, No. 2, 1981, pp. 81-132.

Browne, Thomas; Stable Isotope Techniques in Early Drug Development: An Economic Evaluation, Drug Development, J. Clin. Pharmacol. 1998, vol. 38, pp. 213-220.

Cannon, Joseph; Chapter 19: Analog Design; Burger's Medicinal Chemistry and Drug Discovery, Edited by Manfred Wolff; 1995; pp. 783-802.

Gouyette, Alain; Synthesis of Deuterium-labelled Elliptinium and its Use in Matabolic Studies, Biomedical and Enviornmental Mass Spectrometry, 1988, vol. 15, pp. 243-247.

Haskins, N.J., The Application of Stable Isotopes in Biomedical Research, Biomedical Mass Spectrometry, 1982, vol. 9, No. 7, pp. 269-277.

Shchepinov and Pestov; Isotope Effect, Essential Diet Components, and Prospects of Aging Retardation; Russian Journal of General Chemistry, 2010, vol. 80, No. 7, pp. 1514-1522.

\* cited by examiner

THERAPEUTIC SUBSTANCES THAT MODULATE GENOME METHYLATION

This application claims priority to provisional application No. 61/036,882 filed Mar. 14, 2008 which is incorporated herein by reference.

BACKGROUND

The epigenomic modulation of gene function is well known. Cytosine bases (C) in DNA may be found methylated in the 5 position, and this is used as a signal to reduce expression of the genes in which those bases are located. Enzymes add methyl groups to C de novo to maintain the pattern of methylation through DNA replication.

Epigenetic processes control cell differentiation (allowing cells to maintain different characteristics despite containing identical genes); imprinting; gene silencing; X-chromosome inactivation; reprogramming; the progress of carcinogenesis; etc. Embryonic development, as well as success of cloning and embryonic stem cell (ESC) technologies, depend on the epigenetics. DNA methylation patterns are controlled by DNA methyltransferases, of which DNMT1 is the most abundant. It transfers patterns of methylation to a new strand after DNA replication and is essential for embryonic development, imprinting and X-inactivation [Robertson K D. et al, Nat. Rev. Genet. 2000; 1:11]. Epigenetic patterns "reset" when organisms reproduce.

In mammals, most cells terminally differentiate, and only stem cells retain the ability to differentiate into different cell types. Embryonic stem cells can differentiate into any cell type, thus holding a tremendous potential for regenerative medicine. As embryonic stem cells are difficult to obtain, methods of reprogramming other cells, such as skin cells, to give induced pluripotent stem (iPS) cells are being developed. Current approaches to trick cells into de-differentiation rely on genetic modification [Okita K. et al. Nature 2007; 448: 313]. De-differentiation is based on changes in DNA methylation patterns, so novel methods of affecting the DNA methylation process and erasing the DNA methylation pattern are required. Any method that provides a bias on methylation pattern or its kinetics would be a valuable research tool.

Preferably, such methods should not involve genetic manipulations or immunogenic drugs, which currently represent a major disadvantage of the existing methods—such as immunogenicity, irreversibility of action, toxicity, instability under physiological conditions, etc. [Christman J K Oncogene 2002; 21:5483]. We propose a novel principle of modulating DNA methylation that may be free of these drawbacks, broadening the arsenal of epigenetics R&D tools.

Many diseases are related to changes in gene expression, and therapies, which alter patterns of gene expression, are useful for treating those diseases. Hence, treatments have been proposed which alter the pattern of DNA methylation through inhibiting the methylation or demethylation of DNA by affecting the enzymes concerned, as discussed for example by Yoo et al. (Biochem. Soc. Trans 32 (6): 910-912). The use of methylation inhibitors have been suggested and tested for the treatment of a wide range of diseases, including cancers such as bladder cancer (Zhang et al., Urologic Oncology—seminars and original investigations 24(2): 1520160), haematopoietic cancers (Jost et al., Letters in drug design and discovery 3(4): 242-252).

Epigenetics affects genetic diseases through imprinting, i.e. different epigenetic patterns contributed by the father and mother (Angelman, Prader-Willi syndromes, etc.). Some teratogens exert damage to the fetus by epigenetic mechanisms.

Gene silencing by aberrant methylation of promoter regions of genes critical for normal cellular functions is a hallmark of cancer [Jones P A. et al.; Nat. Rev. Genet. 2002; 3:415], although a small number of genes (about 10%) in cancerous cells are actually hypomethylated compared to normal cells [Ehrich M. et al., PNAS 2008; 105:4844]. Epigenetic carcinogenes (hexachlorobenzene, arsenite), while not being mutagenic, still result in an increased incidence of tumors. Drugs have been developed that affect DNA methylation by inhibiting corresponding enzymes [Yoo C B. et al., Bloch. Soc. Trans. 2004; 32, 910; and refs therein]. This approach has been tested against a wide range of diseases, including cancers such as bladder cancer, haematopoietic cancers, etc. [Jost E. et al., Letters in Drug Design & Discovery 2006; 3:242].

Cytidine analogues unmethylatable at position 5, such as 5-fluoro-cytidine or 5-azacytidine have been suggested as drugs for cancer therapy (for example WO2004050666) and specific analogues which might modulate DNA methylation are disclosed in, WO2006099132, US2006/0205687, and are reviewed by Jones and Taylor (Cell 20:85-93). A-azazytidine has been approved by the U.S. Food and Drug Administration and is being used as a treatment for cancer under the name Decitabine and for the treatment of Myelodysplastic syndrome under the name Vidaza. These analogues all have a different chemical structure from the cytosine present in normal tissues. Other agents that are not cytosine analogues have also been disclosed which alter methylation of DNA, such as those disclosed in WO2005/011661 and WO2005/085196.

A drawback of all such treatments is that they can act to completely block or overwhelmingly enhance DNA methylation. They are therefore likely to have adverse effects on genes other than the target gene whose activity is desired to be modulated, but not necessarily eliminated (as reviewed by Haaf et al., Pharmac. Therap. 65:19-46). The harmful effects can sometimes be avoided by careful adjustment of the dose of the inhibiting drug, but this requires skill, cognizance of patient physiology and variability, and is not always possible.

It is known that the rates of certain chemical reactions are affected by the nature of the isotopes of the atoms in the reacting bonds. In general, bonds terminating in a heavy isotope will be less liable to cleavage than a bond terminating in a lighter isotope. Of particular note is that bonds between hydrogen atoms and other atoms are less liable to breakage if the hydrogen is $^2$H rather than $^1$H. A similar effect is seen when comparing the rate of cleavage of a bond between a carbon atom and another atom, where bonds with $^{13}$C are less liable to cleavage than bonds with $^{12}$C. This is known as the Kinetic Isotope Effect, and is well described. Many isotopes are known to show this effect, as is described in *Isotope effects in chemical reactions*. (C. J. Collins, N. S. Bowman (eds.) 1970). It is known that these effects are also manifest in enzyme-catalysed reactions, as described in Isotope effects on enzyme-catalysed reactions (Cleland, W. W., M. H. O'Leary, and D. B. Northrop (eds.) 1976).

This invention arises from understanding that the inherent drawbacks of methylation modulating drugs may be overcome by using an agent which modulates but which 1) is naturally occurring and therefore not toxic or immunologic, and 2) can partially inhibit the methylation or demethylation of C in controlled ways. This invention describes the use of the kinetic isotope effect to achieve this effect, and its potential use as both a research tool and possible therapy.

SUMMARY

Embodiments of the invention provides compounds which are analogues of cytosine with the 5 or 6 positions (or both positions) substituted with heavy isotopes, or in which the 5 position is substituted with groups containing heavy isotopes, useful for the treatment of diseases in which DNA methylation is a factor or in which activation or repression of gene expression could be beneficial. The invention also provides biochemical precursors of C, which, when incorporated into C through biochemical pathways, give rise to isotope-reinforced derivatives of C.

DETAILED DESCRIPTION OF THE PREFERRED EMBODIMENT

A composition of compounds with the same chemical bonding structure as cytosine or methylcytosine but with a different isotopic composition at key positions will have significantly and usefully different chemical properties from the unsubstituted compound. The composition is not a naturally occurring composition or compound such as cytosine or methylcytosine. The key positions with respect to methylation and demethylation are position 5 of the base ring, and groups attached to position 5 of the base ring, specifically methyl groups so attached. Other key positions are position 6 of the ring, which is involved in the enzymatic mechanism of methylation (as is described in J K Christman, Oncogene 2002 21:5483-5495.

Accordingly, for a composition of compounds comprises a compound Formula (I):

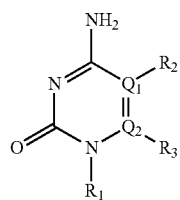

FORMULA (I)

wherein $R_1$ is H, an alkyl, substituted alkyl group, an aryl, substituted aryl group, a sugar, or substituted sugar moiety, a sugar analogue, or a group, which is replaced in vivo by any of these groups, or $R_1$, is a ribose or deoxyribose in a dinucleotide, oligonucleotide, or polynucleotide;
  wherein $R_2$ is $^2H$ or $ZX_3$ where Z may be $^{12}C$ or $^{13}C$ and X may be $^2H$ or $^1H$;
  wherein $R_3$ is $^1H$ or $^2H$;
  wherein $Q_1$ can be $^{12}C$ or $^{13}C$;
with the proviso that at least one atom in $R_2$, $R_3$, $Q_1$ or $Q_2$ is a heavy isotope of the element concerned. The heavy isotopes in the composition are enriched in comparison the naturally occurring compound, which contains a lower proportion of the heavy isotope.

It will be appreciated that the structural formulae above represents the 'Kekule' structure for the molecules, which can also exist in a variety of resonance forms. Thus for example Formula (I) can also be drawn as either of the structures in Formula (II), or as other structures.

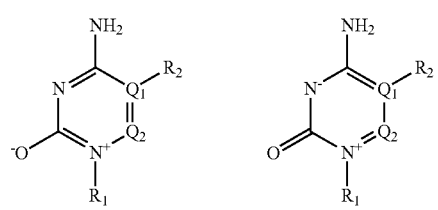

FORMULA (II)

It will be appreciated by one skilled in the art that the terms $^2H$, $^1H$, $^{12}C$ and $^{13}C$ refer to cases where the majority of molecules in a preparation have that isotope in that position in the molecule. Thus the case where Z is $^{12}C$ and all three X are $^2H$ is written as $CD_3$ where D is understood to refer to $^2H$, but there will be in the preparation a minority of molecules where $ZX_3$ is $CD_2H$.

In an embodiment of the invention, $R_2$ is $^2H$ (Deuterium).
In a further embodiment of the invention, $R_2$ is $^{13}C(^1H)_3$.
In a further embodiment of the invention, $R_2$ is $^{13}C(^2H)_3$.
In a further embodiment of the invention, $Q_1$ is $^{13}C$ and $R_2$ is $^2H$.
In a further embodiment of the invention, $Q_2$ is $^{13}C$ and $R_3$ is $^2H$.
In a further preferred embodiment of the invention, $Q_1$ is $^{13}C$, $Q_2$ is $^{13}C$,
  $R_2$ is $^{13}C(^2H)_3$, $R_3$ is $^2H$.
In a further embodiment, $R_1$ is H.
In a further embodiment, $R_1$ is ribose (where the ribose is linked to the aromatic ring through the 1' position).
In a further embodiment, $R_1$ is 5' phosphoribose (where the ribose is linked to the aromatic ring through the 1' position).
In an embodiment of the invention, $R_1$ is deoxyribose, as in Formula (VII)

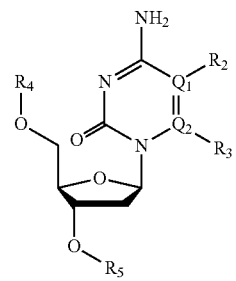

FORMULA (VII)

Where $R_4$ may be H, phosphate, diphosphate, or triphosphate, and $R_5$ may be H, or $R_4$ or $R_5$ or both may be further monomers in a DNA oligonucleotide or polynucleotide.

It will be appreciated that the term 'sugar analogue' includes such compounds as substituted methylcyclopentanes (which are a carbocyclic analogue of ribose), fluorinated sugars and other compounds. It will be appreciated that groups which is replaced in vivo include phosphate, amine, nitro, silyl and other groups which will be cleaved enzymatically or otherwise under physiological conditions to yield a product which can be incorporated into DNA.

Without wishing to be limited by theory, it is expected that compounds of the invention will be incorporated into the DNA of dividing cells in a manner not substantially different from the incorporation of the natural analogues of the compounds of the invention, and once in the DNA they will be methylated (in the case where $R_2$ is $^2H$ (Deuterium) or demethylated (in cases there $R_2$ is a heavy isotope containing analogue of the methyl group) more slowly than the endogenous cytosine, and so modulate the overall genome methylation without completely blocking methylation or demethylation.

It will be appreciated that these embodiments of the invention have subtly different properties that will make them useful for different applications of the invention. Thus an embodiment where $Q_1$ is $^{13}C$, $Q_2$ is $^{12}C$, $R_2$ is $^{12}C(^1H)_3$, $R_3$ is $^1$H will have a lesser effect of reducing the rate of demethylation than an embodiment where $Q_1$ is $^{13}$C, $Q_2$ is $^{13}$C, $R_2$ is $^{13}$C($^2$H)$_3$, $R_3$ is $^2$H.

It will be appreciated that the isotopic composition of other sites in the molecule is not important for the practice of this invention. Thus, the $N_1$ Nitrogen position may be $^{14}$N or $^{15}$N for the practice of this invention, or a mixture of the two. Therefore, an embodiment of the invention is a compound of the structure shown in Formula (III).

A further embodiment of the invention is a compound of the structure shown in Formula (IV).

A further embodiment of the invention is a compound of the structure shown in Formula (V).

A further embodiment of the invention is a compound of the structure shown in Formula (VI).

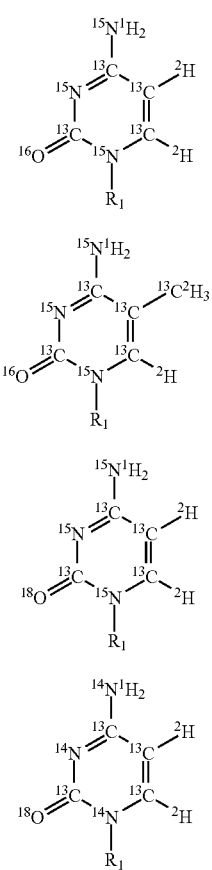

FORMULA (III)

FORMULA (IV)

FORMULA (V)

FORMULA (VI)

A further embodiment of the invention is a compound according to Formula (I) in which every carbon is $^{13}$C.

A further embodiment of the invention is a compound according to Formula (I) in which every nitrogen is $^{15}$N.

A further embodiment of the invention is a compound according to Formula (I) in which every hydrogen atom is a deuterium atom.

A further embodiment of the invention is a compound according to Formula (I) in which every hydrogen atom which does not readily exchange with hydrogen atoms in water when the compound is in solution is a deuterium atom.

It will be appreciated by one skilled in the art that the composition including Formulae (I) through (VI) is materially and significantly different from the cytosine present in living organisms because of the distribution of 'heavy' isotopes within them.

As used herein, the term "sugar," includes ribose or 2'-deoxyribose, which may or may not be phosphorylated on the 5' or 3' end, including a triphosphate group at the 5' end.

The sugar may be subsytitued with one or more "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

Compositions of the invention are expected to be taken up by cells, tissues and organisms under appropriate conditions, as is described by [J. D. Carver, *Acta Paediatr. Suppl.* 1999; 430:83-88], and so will be useful for modulating the methylation of those cells or tissues.

N A further aspect of the invention provides for non-direct ways of incorporating heavy isotope into the right bond positions of cytosine to achieve isotopic enrichment at the desired site by biologic or metabolic processes. For example, one such alternative approach involves supplying biochemical precursors which, when incorporated into 3'-deoxycytidine biosynthesis pathways, yield 3'-deoxy-5-deuterocytidine, 3'-deoxy-6-deuterocytidine, or 3'-deoxy-5,6-dideuterocytidine. Aspartic acid, a non-essential amino acid precursor of the cytidine biosynthesis (through its reaction with carbamoyl phosphate), can be delivered to cells in an appropriate deuterated form (beta-dideutero; alpha-deutero; alpha, beta-trideutero) to provide cytidine derivatives with corresponding deuteration sites. Accordingly, a further embodiment of the invention is the use of commercially available deuterated derivatives of aspartic acid (VIII) to give rise to cytidine derivatives bearing deuterium atoms at pos. 5 and/or 6. Compounds IX and X, when incorporated into cytidine biosynthesis pathway, will result in cytidine incorporating D at pos. 5 (for X) and 6 (for IX), whereas supplementation of compound XI will result in cytidine incorporating deuteriums at pos. 5 and pos. 6.

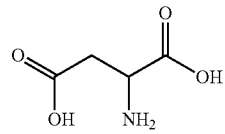

FORMULA VIII

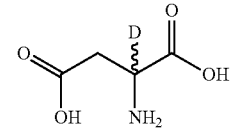

FORMULA IX

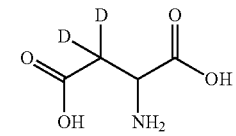

FORMULA X

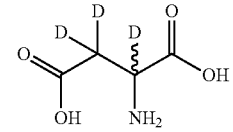

FORMULA XI

A further embodiment of the invention is the use of compounds deuterated as shown on formulae IX-XI, where each carbon atom of the compound is carbon-13.

It is even possible that non specific enrichment of diet with sub-toxic (carbon-13 appears non-toxic in lower animals and deuterium toxicity only first occurs at total heavy water content in the body of >20% in mammals) levels of heavy isotope can achieve significant modulation effects on methylation.

It is expected that partial or transient reduction of methylation can be achieved, apart from the dosage, by combinations of isotopes used; the strength of the effect is expected to increase in the following order of the isotope substitutions: $^{12}C,H, <^{13}C,H, <^{12}C,D, <^{13}C,D$.

It will be appreciated by one skilled in the art that the degree of substitution of the "reinforced" cytosine (Formula I), or cytosine precursors (Formulae IX-XI) for cytosine necessary to change the epigenetic pattern may be as low as 5-10% [Jones P A. et al., Cell 1980; 20:85], due to the "walking" mechanism of the DNA methylases [Drahovsky D. et al., J. Mol. Biol. 1971; 57:475].

A further embodiment of the invention is the use of this approach in combination with histone deacetylase inhibitors [Belinsky S A. et al., Cancer Res. 2003; 63:7089] for synergistic gene reactivation.

One aspect of this invention provides for compounds of Formula I or Formulae IX-XI.

Another aspect of the invention provides for the use of compounds of Formulae (I; IX-XI) as a treatment for a disease characterized by changes in or defects of gene activity. Examples of such diseases are cancer, pre-cancerous states such as myelodysplastic syndrome, juvenile polyposis or solar keratoses, epithelial dysphasia in a variety of tissues, and inflammatory diseases such as rheumatoid arthritis, proriasis, asthma, ectopic dermatisis (eczema), and atherosclerosis.

A further aspect of the invention provides for the use of a compound according to Formulae (I: IX-XI) for the treatment of diseases with epigenetic etiology, such as Fragile X syndrome, Angelman syndrome, Prader-Willi syndrome and Rett syndrome.

A further aspect of the invention provides for the use of a compound according to Formulae (I; IX-XI) for the treatment of diseases which can be affected by changes in gene activity. Examples of such diseases are thallasemia and sickle cell anemia.

A further aspect of the invention provides for the methods and use of a compound of the invention for the modulation of cell growth or differentiation. A preferred embodiment of this aspect of the invention is the use of compositions for the modulation of the growth, pluripotency or differentiation of stem cells. This transient reduction of methylation can be used to obviate the need for one or more of the transcription factors needed for reprogramming.

A further aspect of the invention provides for the use of a composition for modulation of DNA methylation in tissue, organ or organisms cloning.

Methods include administering the composition to subjects. Subjects may include, mammals such as humans, livestock and laboratory animals, such as mice rats, rabbits monkeys or other lower order animals.

A further aspect of the invention provides for enhanced reprogramming efficiencies when the transient reduction of methylation is used in combination with a standard stem cell reprogramming cocktail of containing transcription factors oct4, /sox2, /myc, and /klf4 viruses/plasmids in appropriate delivery vehicles [Takahashi K et al, Cell 2006; 126:663-676; and Qi H et al, Cell Res 2007; 17:578-580].

A further aspect of the invention provides a pharmaceutical composition of the compound of the invention, as a typical medium for cell growth comprising a standard medium, such as a Dulbecco/Vogt modified Eagle's (Harry Eagle) minimal essential medium (DMEM) or Roswell Park Memorial Institute medium (RPMI), without cytidine; and an additive system that comprises a 3'-deoxycytidine nucleoside; or 3'-deoxycitidine 5'-phosphate; or 3'-deoxycitidine 5'-triphosphate of the stable isotope reinforced type described by Formula I in amounts sufficient in combination to promote cell grows in the medium.

Preferably, the nucleoside or nucleotide will be added in the range of 0.5 to about 2000 milligrams per liter of the medium.

More preferably, the isotope reinforced cytosine derivative (Formula I) will be added in the range of about 10 to 500 milligrams per liter of the medium.

In a different embodiment of the invention, a typical medium for cell growth comprising a standard medium, such as a Dulbecco/Vogt modified Eagle's (Harry Eagle) minimal essential medium (DMEM) or Roswell Park Memorial Institute medium (RPMI), without aspartic acid; and an additive system that comprises the stable isotope reinforced type described by Formula IX-XI in amounts sufficient in combination to promote cell grows in the medium.

Preferably, the aspartic acid derivative will be added in the range of 0.5 to about 2000 milligrams per liter of the medium.

More preferably, the isotope reinforced aspartic acid derivative (Formula IX-XI) will be added in the range of about 10 to 1000 milligrams per liter of the medium.

A pharmaceutical composition containing the active ingredient may be in a form suitable for oral use, for example, as tablets, troches, lozenges, aqueous or oily suspensions, oil-in-water emulsions, dispersible powders or granules, emulsions, hard or soft capsules, or syrups or elixirs. Such compositions may contain excipients such as bulking agents, solubilization agents, taste masking agents, stabilisers, colouring agents, preservatives and other agents known to those ordinarily skilled in the art of pharmaceutical formulation.

A pharmaceutical composition containing the active ingredient may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

A pharmaceutical composition may also be suitable for delivery by inhalation to the nose, throat or lungs. Such compositions may be prepared by pre-forming compounds of the invention into particles suitable for inhalation together with other materials, or dissolving compounds of the invention in a material suitable for forming an aerosol.

A pharmaceutical composition may also be suitable for delivery by topical application, as a spray, cream, ointment, lotion, or as a component or additive to a patch, bandage or wound dressing. In addition the compound can be delivered to the site of the disease by mechanical means, or targeted to the site of the disease through the use of systemic targeting technologies such as liposomes (with or without chemical modification that provides them with affinity for the diseased tissue), antibodies, aptamers, lectins, or chemical ligands with affinity for aspects of the diseased tissue that are less abundant or not present on normal tissue.

A pharmaceutical composition of the invention may also be in a form suitable for administration by injection. Such compositions may be in the form of a solution, a suspension or an emulsion. Such compositions may include stabilizing agents, antimicrobial agents or other materials to improve the function of the medicament. This invention also encompasses dry, dessicated or freeze-dried forms of compounds of the invention which can readily be formed or reconstituted into a solution suspension or emulsion suitable for administration by injection, or for oral or topical use.

EXAMPLES

There are literature examples for substitutions at any position for all major nucleotide bases, with all major types of isotopes ($^2H_2$, $^3H_2$, $^{13}C$, $^{14}C$, $^{15}N$, $^{18}O$ etc.). Described below are just two procedures, based on the previously published work, for selective deuteration of nucleosides [Esaki et al., Heterocycles 2005; 66:361-369, and Chiriac et al., Labelled Compd. Radiopharm. 1999; 42:377-385]. Numerous other protocols are suitable as well. It is often possible to exchange hydrogens for deuteriums on an existing nucleic acid base/nucleoside, while to incorporate $^{13}C$, the bases should be assembled (for example, see [Folesi et al., Nucleosides Nucleotides Nucleic Acids 2000]).

Example 1

5-D-Deoxycytidine from Deoxycytidine

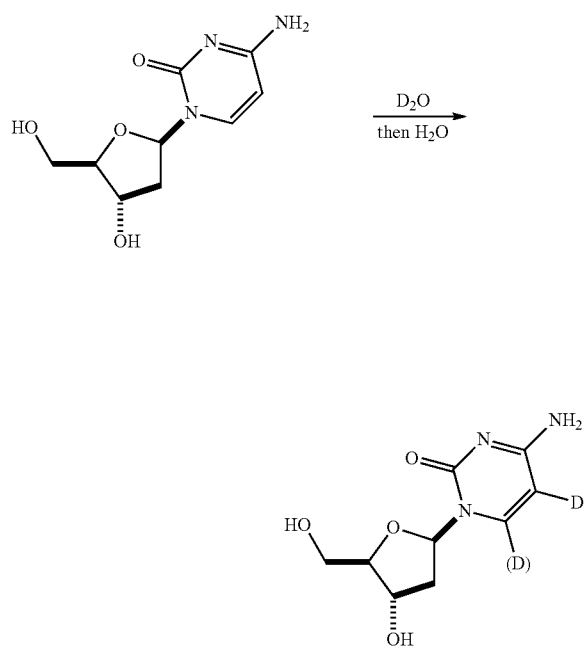

Deoxycytidine (227 mg, 1 mmol, Aldrich) was dissolved in 4 ml of $D_2O$. 10% Pd/C (27 mg, 10 wt % of the substrate, Aldrich) was added, and the mixture was stirred at 160° C. in a sealed tube under $D_2$ atmosphere for 24 h. After cooling to RT, the reaction mixture was filtered using a membrane filter (Millipore Millex®—LG). The filtered catalyst was washed with boiling water (150 ml), and the combined aqueous fractions were evaporated in vacuo, and then again dissolved in $H_2O$ and evaporated (5×25 ml) to give 5-D-deoxycytidine as a white solid (206 mg). The structure of the nucleoside was confirmed by MALDI-TOF (Voyager Elite, PerSeptive Biosystems), with HPA as a matrix. Found: 228.225 (45%; MI); 229.229 (27%; Double-deuterated product; MI).

Example 2

5-D-Deoxycytidine from 5-Bromodeoxycytidine

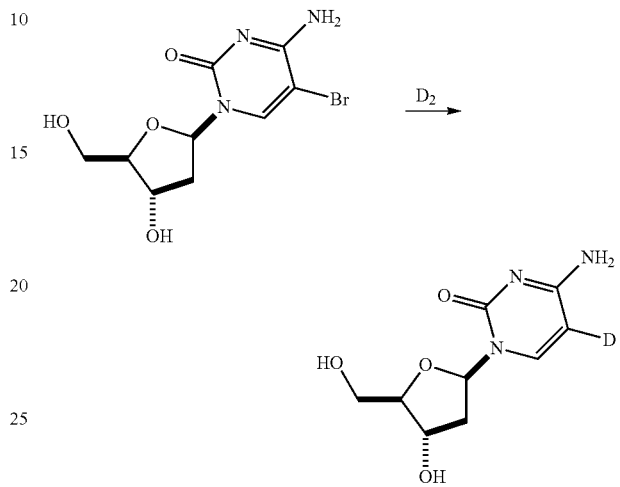

A suspension of 500 mg of 7% Pd/C catalyst (prepared from $PdCl_2$ as described in [Chiriac et al., 1999; 42:377-385]) in 8 mL of acetic acid-d, (DOAc) was stirred vigorously for 20 min. in a deuterium atmosphere with intermittent bubbling of deuterium gas through the mixture. 5-Bromo-2'-deoxycytidine (307 mg, 1 mmol, Carbosynth, UK), converted into its benzoyl derivative using 3 equivalents of benzoyl chloride as described in [M. J. Gait, Oligonucleotide Synthesis. A Practical Approach, IRL Press, 1984], was added and the mixture was stirred vigorously for 5 h at room temperature under 1 atm pressure of $D_2$ and then filtered. 410 mg (5 mmol) of NaOAc was added to the filtrate, and the solution evaporated in vacuo. The residue was treated with 10 mL of $CHCl_3$, and 5 mL of $H_2O$ and the organic layer was separated. The aqueous phase was extracted with 2×10 mL of chloroform. The combined organic phase was washed with 10 mL of water, dried over $Na_2SO_4$, filtered, and evaporated. The resulting residue was suspended in 3 ml saturated aqueous ammonia and was allowed to stand for 24 h at rt and then was evaporated. The residual pale yellow foam was dissolved in water and applied to a column of 10 mL of Dowex 1-X2 (OH—) resin. The column was washed with 500 mL of water, 1000 mL of 3M MeOH/water, and then was eluted with 500 mL of 0.5% HOAc/water. Appropriate fractions were pooled and evaporated in vacuo. The residue was dissolved in a minimum volume of MeOH, diluted with dry benzene, and lyophilized to give mg (83%) of the title compound as a pale yellow powder. The structure of the nucleoside was confirmed by MALDI-TOF (Voyager Elite, PerSeptive Biosystems), with HPA as a matrix. Found: 228.195 (53%; MI). In this procedure, other reducing agents, such as $NaBD_4$, can also be employed.

What is claimed is:

1. A method of reducing DNA methylation comprising administering to a subject in need thereof, a compound of Formula (I):

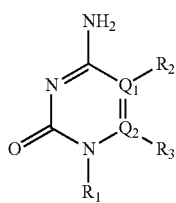

Formula (I)

wherein $R_1$ is H, a sugar or substituted sugar moiety, a sugar analogue, or a group which is replaced in vivo by the sugar or substituted sugar moiety or the sugar analogue;

wherein $R_2$ is $^2H$ or $ZX_3$ where Z may be $^{12}C$ or $^{13}C$ and X may be $^2H$ or $^1H$;

wherein $R_3$ is $^1H$ or $^2H$;

where $Q_1$ and $Q_2$ can be $^{12}C$ or $^{13}C$; and with the provision that at least one atom in $R_2$, $R_3$, $Q_1$ or $Q_2$ is a heavy isotope;

wherein the $^{13}C$, $^2H$ or both are enriched at least 20% more individually or collectively in comparison to naturally occurring $^{13}C$, $^2H$ or both at the same position in the compound, or a pharmaceutically acceptable salt of a compound of Formula (I);

wherein the compound of Formula (I) is incorporated into the subject's DNA as an isotopically modified compound following administration;

wherein the compound of Formula (I) is administered to the subject in need thereof in an amount that reduces DNA methylation such that harmful disease effects are mitigated.

2. The method of treatment of claim 1 wherein the diseases are cancers, precancerous states, or inflammatory diseases.

3. The method of claim 1 wherein the heavy isotope is enriched greater than 50% in comparison to a naturally occurring amount.

4. The method of claim 1 wherein the heavy isotope is enriched greater than 2X in comparison to a naturally occurring amount.

5. The method of claim 1 wherein the heavy isotope is enriched greater than 5X in comparison to a naturally occurring amount.

6. The method of claim 1 wherein the heavy isotope is enriched greater than 10X in comparison to a naturally occurring amount.

7. The method of claim 1 wherein the heavy isotope is enriched greater than 100X in comparison to a naturally occurring amount.

8. The method of claim 1, wherein the compound of Formula (I) is incorporated into the subject such that at least 5% of the subject's cytosine is substituted with an isotopically modified compound.

9. The method of claim 8, wherein at least 10% of the subject's cytosine is substituted with an isotopically modified compound.

10. The method of claim 8, wherein the compound of Formula (I) is incorporated into the subject's diet.

11. The method of claim 10, wherein the subject is a human.

12. The method of claim 8, further comprising: administering a precursor to the compound of Formula (I) to the subject in need thereof, wherein the precursor is a non-essential amino acid precursor of cytidine biosynthesis that is isotopically substituted;

wherein the subject produces the compound of Formula (I) from the precursor by the cytidine biosynthesis pathway;

wherein the compound of Formula (I) is incorporated into the subject's DNA.

13. The method of claim 12, wherein the precursor is substituted with deuterium and the cytidine biosynthesis pathway is the 3'-deoxycytidine biosynthesis pathway.

14. The method of claim 13, wherein the precursor is a deuterated form of aspartic acid selected from the group consisting of Compounds of Formula IX, X and XI,

FORMULA IX

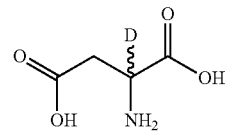

FORMULA X

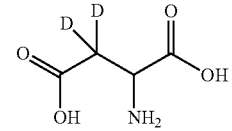

FORMULA XI

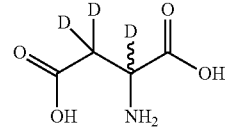

wherein the precursor contains heavy isotope at a level of greater than 20% higher than that of naturally occurring compounds.

* * * * *